US008237929B2

(12) United States Patent
Myrick et al.

(10) Patent No.: US 8,237,929 B2
(45) Date of Patent: *Aug. 7, 2012

(54) SIGNAL PROCESSING FOR OPTICAL COMPUTING SYSTEM

(75) Inventors: Michael L. Myrick, Irmo, SC (US); Robert P. Freese, Pittsboro, NC (US); William Soltmann, Columbia, SC (US); David L. Perkins, Irmo, SC (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/196,802

(22) Filed: Aug. 2, 2011

(65) Prior Publication Data

US 2012/0026484 A1 Feb. 2, 2012

Related U.S. Application Data

(63) Continuation of application No. 12/447,595, filed as application No. PCT/US2007/083293 on Nov. 1, 2007, now Pat. No. 7,990,538.

(60) Provisional application No. 60/856,192, filed on Nov. 2, 2006.

(51) Int. Cl.
*G01N 21/00* (2006.01)
(52) U.S. Cl. ...................................................... 356/437
(58) Field of Classification Search .................... None
See application file for complete search history.

(56) References Cited

U.S. PATENT DOCUMENTS 6,347,131 B1 * 2/2002 Gusterson ...................... 378/54
2002/0109094 A1 * 8/2002 Goetz et al. .............. 250/339.11

* cited by examiner

*Primary Examiner* — Tu Nguyen
(74) *Attorney, Agent, or Firm* — Haynes and Boone, LLP

(57) ABSTRACT

The present subject matter relates to methods of high-speed analysis of product samples during production of the product. Light is directed to a portion of a product under analysis and reflected from or transmitted through the product toward optical detectors. Signals from the optical detectors are compared to determine characteristics of the product under analysis. Temperature within the monitoring system may be monitored in order to provide compensation for the signals produced by the optical detectors. The products under analysis may be stationary, moved by an inspection point by conveyor or other means, or may be contained within a container, the container including a window portion through which the product illuminating light may pass.

19 Claims, 1 Drawing Sheet

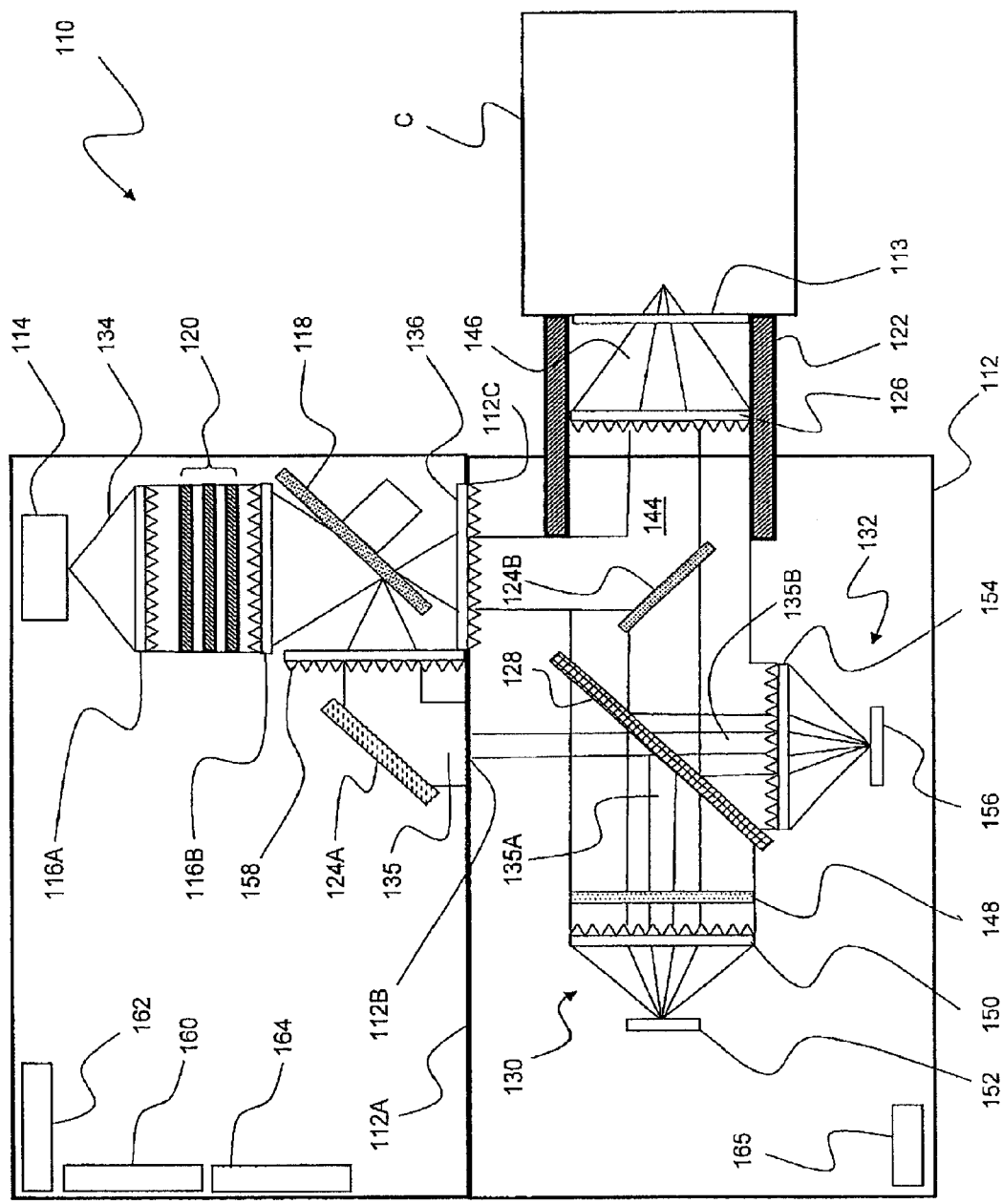

SIGNAL PROCESSING FOR OPTICAL COMPUTING SYSTEM

The present application is a continuing application of, and claims priority to, U.S. application Ser. No. 12/447,596 filed Feb. 8, 2010 now U.S. Pat. No. 7,990,538, issued on Aug. 2, 2011, which claims priority to PCT/US2007/083293 with an international filing date of Nov. 1, 2007, which claims priority to U.S. Patent Application Ser. No. 60/856,192 filed on Nov. 2, 2006.

FIELD OF THE INVENTION

The present subject matter relates to system design, fabrication and operation of multivariate optical elements. More particularly, the present subject matter relates to methodologies of using multivariate optical computing systems to illuminate a sample such that information about the sample can be analyzed from reflected or transmitted light in real time or near real time.

BACKGROUND OF THE INVENTION

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, measurement of light intensity may be difficult to convert to information due to contained interfering data. That is, several factors may contribute to the intensity of light, even in a relatively restricted wavelength range. It is often impossible to adequately measure the data relating to one of these factors since the contributions from other factors may be unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information regarding the sample's ethylene content. Light from each of several samples may be directed to a series of bandpass filters which separate predetermined wavelength bands from the light. Light detectors following the bandpass filters measure the intensity of each light bald. If the ethylene content of each polymer sample is measured using conventional meals, a multiple linear regression of ten measured bandpass intensities against the measured ethylene content for each sample may produce all equation such as:

$$y = a_0 + a_1 w_1 + a_2 w_2 + \ldots + a_{10} w_{10} \quad \text{(``Equation 1'')}$$

where y is ethylene content, $a_n$, are constants determined by the regression analysis, and $w_n$, is light intensity for each wavelength bald.

Equation 1 may be used to estimate ethylene content of subsequent samples of the same polymer type. Depending oil the circumstances, however, the estimate may be unacceptably inaccurate since factors other than ethylene may affect the intensity of the wavelength bauds. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a line-algebraic process known as singular value decomposition (SVD). SVD is at the heart of principal component analysis, which should be well understood by those of ordinary skill in this art. Briefly, however, principal component analysis is a dimension reduction technique, which takes m spectra with n independent variables and constructs a new set of eigenvectors that are linear combinations of the original variables. The eigenvectors may be considered a new set plotting axes. The primary axis, termed the first principal component, is the vector, which describes most of the data variability. Subsequent principal components described successively less sample variability, until only noise is described by the higher order principal components.

Typically, the principal components are determined as normalized vectors. Thus, each component of a light sample may be expressed as $x_n z_n$, where $x_n$, is a scalar multiplier and $z_n$ is the normalized component vector for the $n_{th}$, component. That is, $z_n$, is a vector in a multi-dimensional space where each wavelength is a dimension. As should be well understood, normalization determines values fox—a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. Thus is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other thee dimensions provides redundant data, since this magnitude is already contributed by two or more of the orthogonal axes.

Because the principal components are orthogonal, or perpendicular each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the sane principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$, of these components in one sample might be J, K, L, and M, whereas in the next sample the magnitudes may be 0.94 J, 1.07K, 1.13 L and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y = a_0 + a_1 x_1 + a_3 x_3 + a_4 x_4 \quad \text{(``Equation 2'')}$$

where y is octane rating, a, are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$, corresponding to the component vector, and if the resulting weighted principal components are summed by wavelength, the regression vector takes the following form:

$$y = a_0 + b_1 u_1 + b_2 u_2 + \ldots + b_n u_n \quad \text{(``Equation 3'')}$$

where y is octane rating, $a_o$ is file first regression constant from Equation 2, $b_n$ is the sum of the multiple of each regression constant $a_n$ from Equation 2 and the value of its respective normalized regression vector at wavelength n, and $u_n$, is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance aid the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing WOC) is a powerful predictive spectroscopic technique that incorporates a multi-wavelength weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multi-variate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or co-adds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

While various implementations of Optical Analysis Systems have been developed to enhance measurement accuracy, no design has emerged that generally encompasses all of the desired characteristics as hereafter presented in accordance with the subject technology.

SUMMARY OF THE INVENTION

In view of the recognized features encountered in the prior art and addressed by the present subject matter, a method of high-speed processing and monitoring of a plurality of sample portions of products has been developed. In accordance with an exemplary configuration a plurality of portions of pharmaceutical product may be moved past an inspection point where at least one portion of the pharmaceutical product is illuminated with a spectral-specific light through an optic window. The window may be configured to focus the spectral-specific light onto a portion at the inspection point. Reflected light carrying information about the portion through at least one multivariate optical element falling on a first detector produces a first signal. A portion of the spectral-specific light is deflected toward a second detector, and at least one selected property of the portion is determined at high speed based upon the detector outputs as the portion moves past the inspection point. The disclosed method also includes measuring and recording the temperature of the system to enable compensation or correction of the detector outputs based on the system temperature.

The product portions may correspond to pharmaceutical tablets, Ways or other containers of powders, or partially- or fully-enclosed sample containers that are at least partially transparent to light focused onto the portion. The product portions may be moved past the inspection point at a rate between about one portion/second and about five portions/second, with the monitoring occurring in real-time at high speeds.

In another aspect of the invention, a method of high-speed processing and monitoring includes moving a product past an inspection point; illuminating at least a portion of the product with a light; directing light carrying information about the portion through at least one multivariate optical element to produce a first signal; detecting the first signal at a first detector; detecting a deflected portion of the light at a second detector; and determining at high speed at least one selected property of the portion as the portion moves past the inspection point based upon the detector outputs. This aspect of the invention also includes measuring and recording the temperature of the system to enable compensation or correction of the detector outputs based on the system temperature. The product in this aspect may be a pharmaceutical tablet, a pharmaceutical powder, a food product, a chemical, a liquid, a gas, an emulsion, a solution, and/or a mixture.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which:

FIG. 1 illustrates an exemplary embodiment of a real time measurement system in accordance with the present technology.

Repeat use of reference characters throughout the present specification and appended drawings is intended to represent same or analogous features or elements of the invention.

DETAILED DESCRIPTION OF THE INVENTION

As discussed in the Summary of the Invention section, the present subject matter is particularly concerned with an improved methodology for high-speed processing and monitoring of a plurality of sample product portions.

Selected combinations of aspects of the disclosed technology correspond to a plurality of different embodiments of the present invention. It should be noted that each of the exemplary embodiments presented and discussed herein should not insinuate limitations of the present subject matter. Features or steps illustrated or described as part of one embodiment may be used in combination with aspects of another embodiment to yield yet further embodiments. Additionally, certain features may be interchanged with similar devices or features not expressly mentioned which perform the same or similar function.

As used herein, the term "light" is broadly used to mean any form of radiation or radiative energy including, but not limited to, visible light or light in the infrared region. "Light" is also referred to herein as a light signal, a light beam, a light ray and the like to mean any form of radiative energy in the electromagnetic spectrum. Similarly, the term "transmission" can mean transmission of radiative energy onto a surface of a sample; Penetration, however slight, into a sample such as a particulate sample or opaque fluid sample; or passage through a sample.

Further, as used herein, the sample being evaluated can be a solid or a fluid including, but not limited to, a powder, a pharmaceutical powder mixed with lactose and other excipient materials, a chemical, a polymer, a petroleum product, a solution, a dispersion, an emulsion and combinations of these solids and fluids.

Reference will now be made in detail to the presently preferred embodiments of the subject optical computing system. Referring now to the drawings, FIG. 1 illustrates an optical analysis system 110 generally depicting the concept of the present subject matter. As shown in FIG. 1, optical analysis system 110 broadly includes a housing 112, an illumination or light source 114, a chopper wheel 118, one or more spectral elements 120, a focusing lens 126, a beam splitter 128, a first detector 130 including a multivariate optical element 148, and second detector 132. Optical analysis system 110 further includes representatively illustrated electrical connection 160, pressurization sensor 162 and purge gas assembly 164. These representatively illustrated components are well understood by those of ordinary skill in the present art and, therefore, further description is not deemed necessary to understand and practice these aspects of the present subject matter.

With more particular reference to FIG. 1, illumination source 114 provides light 134, which passes through collecting Fresnel lens 116A and into and through spectral element (s) 120. In an exemplary configuration, illumination source 114 may be rated for at least about 10,000 hours of operation, which alleviates a need for redundant. Illumination sources through such redundant sources may be provided if desired. Further, in the illustrated exemplary configuration, collecting Fresnel lens 116A may be sized to be about 1.5 square inches and spaced about 0.6 inches from illumination source 114. Those of ordinary skill in the art will appreciate that these dimensions can be adjusted according to particular system requirements and are thus not meant as limitations of the present subject matter.

As further shown in FIG. 1, light 134 passes through spectral elements 120, which filter out undesired wavelengths to define a desired spectral region in order to target a particular chemical material of interest. In an exemplary configuration the spectral region may correspond to, 1500-2000 nm. Light 134 is focused by focusing Fresnel lens 116B, which, in an exemplary configuration may also be sized to be about 1.5 square inches and spaced about 1 inch from the chopper wheel 118. As shown, the chopper wheel 118 reflects a portion of light 134 as a calibration or reference light 135 and passes another portion as transmitted light 144.

Calibration light 135 is collimated by lens 158 before reflecting from a first Mirror 124A through an adjustable aperture 112B in a bulkhead 112A of the housing 112. Aperture 112B is adjustable to control tile amount of the calibration light 135 passing through the aperture. Finally, calibration light 135 impinges on beam splitter 128 thereby sending a portion 135A of calibration light 135 to the first MOE detector 130 and a portion 135B of calibration light 135 to the second or baseline detector 132.

With further reference to FIG. 1, it may be seen that transmitted light 144 passes from the chopper wheel 118 into collimating Fresnel lens 136, which in this exemplary configuration may be sized to be about 1.5 square inches and spaced about 0.6 inches from the chopper wheel 118. Transmitted light 144 passes through another adjustable aperture 112C in the bulkhead 112A and impinges upon a second mirror 124B, which directs transmitted light 144 toward a sample in a container C. In an exemplary configuration, container C may correspond to a mixing vat or blender. Those of ordinary skill in the art will appreciate that "container" C could correspond to a conveyor belt or other device for holding or transporting the sample and is thus not limited to an enclosed container.

As further illustrated in FIG. 1, transmitted light 144 is focused by focusing Fresnel lens 126, which in this exemplary configuration may be round and about $^{15}/_{16}$ inches in diameter and is adjustable with an inner tube 122. Also in this exemplary configuration, lens 126 may be positioned about 0.6 inches from an outer surface of the container C. As shown, transmitted light 144, now focused by Fresnel lens 126, passes through a transmissive window 113. In an exemplary configuration transmissive window 113 may be approximately 1 inch in diameter and include an anti-reflective (AR) coating disposed on one or both sides of the window 113. The AR coating ensures that the chemical process in the container C does not interfere with the measuring process of optical analysis system 110. Thus, transmitted light 144 enters the container C and reflects from the sample as carrier light 146. The sample can be a moving mixture such as aspirin and an excipient being blended in real time, or a plurality tablets passing by on a conveyor belt at high speed.

Referring further to FIG. 1, it will be seen that carrier light 146 is directed by the tube 122 in a direction of the first detector 130. Eventually, carrier light 146 impinges on beam splitter 128 so that portion of carrier light 146 passes in a direction of detector 132 for baselining with portion 135B of calibration light 135. Another portion of carrier light 146 passes through MOE 148, which as noted above, has been selected for the chemical of interest based on the various components of the system 110. Finally, that portion of carrier light 146, having passed through the MOE 148, is focused by lens 150 and received by the detector 152. As described above, the two signals collected by the detectors 152 and 156 can be manipulated, e.g., mathematically, to extract and ascertain information about the sample carried by the carrier light 146.

Temperature sensor 165 is positioned within housing 112 as illustrated in FIG. 1 and may be used to measure and record the temperature of the system. By measuring the system temperature, a known calibration of detector response to system temperature can be applied to the detector outputs. Changes in system temperature are thus compensated for in the system output.

The functionality of the MOC system 110 and improvements as described above allows for the collection of the entire spectral range of testing simultaneously, that is, dynamic real-time detection and measurement may be provided. This fact is notably different than either a system based on either a scanning lamp or detector system or a discrete diode array detection system. The ability to monitor over the complete spectral range of interest opens up a re-definition of the term "real-time" measurement and analysis.

For instance, true real-time process measurements are possible. In the context of the present disclosure, "real time" is intended to refer to obtaining data without delays attendant to collecting samples or delays due to lengthy computer processing of measurement signals. In accordance with the present technology, process data can be obtained in an instantaneous or near-instantaneous manner through using the disclosed measurement techniques to directly monitor materials of interest while such materials are undergoing process steps. Long delays due to processing of measurement signals are avoided by optically processing the light as it is reflected from the material(s) of interest.

Although specific examples disclosed herein present monitoring the blending of powdered material and examining solid tablets, the general concept can be extended to other phases. Non-limiting examples of such include use of the present system in analyzing solids, solutions, emulsions, gases, and dispersions. In addition, while exemplary embodiments discussed herein use reflectance measurements, measurements in a transmission or transflectance mode would also be appropriate.

One of ordinary skill in the art will recognize that differing applications may require modifications and alterations to certain components in order to take full advantage of the presently-disclosed systems. For instance, more diffusion of light has been observed in solid powders relative to liquids; accordingly, different lenses may be needed when a liquid is monitored in order to account for such variations and achieve more accurate measurements.

The presently-disclosed technology can be applied to real-time measurements for a range of industrial applications. These include, but are not limited to monitoring of the blending of pharmaceutical powders, including excipients, additives, and active pharmaceutical materials; blending of other powders, including food and chemicals; monitoring dispersions and bi-phasic mixtures (such as insulin, emulsions); and oil and gas applications, including analyzing water content in oil, or oil content in water.

Inclusion of a transmissive window provides physical separation between the measuring device and the process or material being tested. Therefore, this window allows for in-line measurement and/or non-invasive measurement of parameters such as chemical functionality, including alcohol content of petroleum fractions or trackifier resins. Environmental applications are also conceivable, such as stack gas analysis, including measurement of NOx, SOx, CO, CO2, or other gases in a gas stream; wastewater analysis and treatment monitoring; and hazardous substance monitoring applications such as mercury vapor detection.

As previously noted, MOC technology in accordance with the present subject matter may be used to monitor a wide variety of materials as the materials are subjected to different processes. In an exemplary configuration, the mixing of powders can be monitored. As materials are blended, the existing art does not allow for continuous, real-time in-line measurement. Current limitations are the result of several factors including: moving of the powders being measured during the course of data acquisition and the need to connect analytical equipment to the measurement point using fiber optic cables. The optical analysis system in accordance with the present technology is designed to allow for instantaneous measurement using a measurement point located on the vessel.

Other exemplary embodiments of the present subject matter provide real time measurement of flowing materials. In such embodiments, sampling window(s) may be located on a pipe or vessel such that interrogating illumination may be applied to the material. For instance, a port may be included on a pipe to allow for sampling of the material inside the pipe. The window may be positioned directly on the pipe, or on a small diversion away from the main flow path, as appropriate under the circumstances. Such embodiments could also include sampling of vapor systems within a stack to monitor combustion gases or flowing process stream such as water containing other materials.

Still further embodiments of the present subject matter include the real time Measurement of materials containers, such as vials or bins where the container is either at least partially open to the outside environment or transmissive to the sampling illumination. Such containers could be stationary or in motion. A container could also include a conveyor or trough carrying material. Typical applications include monitoring the progress of a chemical reaction or the content of samples moving past a measurement location.

The present subject matter may be better understood from the following tests and examples. In a first example, a breadboard system was constructed and used to test a mixture of powders. The first system components included a 20 W Gilway lamp and employed a 5 mm deuterium oxide ($D_2O$) and 5 mn Germanium spectral elements. A fiber optic probe was employed as an optical window while a InAr detector was used for measurements. For this example, a powdered sample with a known composition was placed in a dish and the fiber optic probe was placed in contact with the powder. The output of the detectors was monitored and recorded.

In a second example, a system was constructed and used to make static measurements on aspirin/lactose. The second example system employed components identical to those of the first sample except for the detector where a PbS detector from New England Photoconductor was employed instead of the InAr detector. For this example, a powdered sample with a known composition was placed in a dish and the system light beam was focused on the powder. The output of the detectors was monitored and recorded. Aspirin/lactose samples covering the range of 100% aspirin to 100% lactose were tested.

In a third example, a system similar to that employed ill the second example was employed except that a sapphire window was employed to gain access to the test material light borne data. In this example, Aspirin/Lactose testing was performed using a mixer bowl containing lactose and the system measured as aspirin was added to the system and mixed. Specifically, lactose powder was placed in the bowl of a mixer and the measurement system was attached the bowl using a Swagelok® brand fitting. A sapphire window was used to contain the powder in the bowl and allow the system to interrogate the powder. With the mixer turning, known amounts of aspirin were added and the system output signal was monitored and recorded. Aspirin was added in several allotments to about 37% final aspirin concentration.

Although the invention has been described in such a way as to provide an enabling disclosure for one skilled in the art to make and use the invention, it should be understood that the descriptive examples of the invention are not intended to limit the present invention to use only as shown in the figures. For instance, the housing can be shaped as a square, an oval, or in a variety of other shapes. Further, a variety of light sources call be substituted for those described above. It is intended to claim all such changes and modifications as fall within the scope of the appended claims and their equivalents. Thus, while exemplary embodiments of the invention have been shown and described, those skilled in the art will recognize that changes and modifications may be made to the foregoing examples without departing from the scope and spirit of the invention.

What is claimed is:

1. A method for downhole analysis of samples in a wellbore, comprising:
   providing an illumination source downhole;
   illuminating with a portion of the light from the illuminating source at least a portion of a sample with light at an inspection point;
   providing first and second light sensitive detectors, the detectors producing output signals based on received light;
   directing a portion of the light from the illuminated sample portion toward the first and second light sensitive detectors, the light from the illuminated sample portion carrying information about the sample portion;
   directing at least a portion of the light from the illumination source toward the first and second light sensitive detectors as a reference light;
   providing a temperature sensor in proximity to the first and second light sensitive detectors, the temperature sensor producing an output signal based on temperature;
   compensating the output signals produced by the first and second detectors based on the temperature output signal; and
   analyzing the compensated output signals produced by the first and second light sensitive detectors to determine temperature compensated illuminated sample portion information.

2. The method of claim 1, wherein the sample is at least one of a pharmaceutical tablet, a pharmaceutical powder, a food material, a chemical, a liquid, a gas, an emulsion, a solution, or a mixture thereof.

3. The method of claim 1, wherein the sample is a hydrocarbon mixture in a closed container, the container being at least partially transparent to the illuminating light.

4. The method of claim 1, further comprising: moving the sample past the inspection point.

5. The method of claim 1, wherein directing light from the sample portion comprises directing light reflected from the sample portion.

6. The method of claim 1, wherein directing light from the sample portion comprises directing light transmitted through the sample portion.

7. The method of claim 1, wherein illuminating comprises illuminating the sample with a spectral-specific light.

8. The method of claim 7, further comprising: illuminating the sample through an optic window, the optic window being configured to focus the spectral-specific light onto a sample portion at the inspection point.

9. The method of claim 1, wherein the sample comprises a plurality of discrete portions.

10. The method of claim 9, wherein the plurality of discrete portions are disposed in closed containers, the containers at least partially transparent to the spectral-specific light.

11. The method of claim 1, further comprising passing light directed toward one of the light sensitive detectors through a multivariate optical element.

12. The method of claim 1, further comprising modulating light from the illumination source.

13. The method of claim 1, further comprising creating a vacuum around the light sensitive detectors and measuring the temperature within the vacuum.

14. The method of claim 1, further comprising splitting the directed light from the illuminated sample into two sample beams, and directing one sample beam to the first detector and the other sample beam to the second detector.

15. The method of claim 14, further comprising:
   splitting the reference light into two reference beams, and directing one reference beam to the first detector and the other reference beam to the second detector; and
   passing one reference beam and one sample beam through a multivariate optical element.

16. A method for downhole analysis of samples in a wellbore, comprising:
   providing an illumination source downhole;
   illuminating with a portion of the light from the illuminating source at least a portion of a sample at an inspection point;
   providing first and second light sensitive detectors, the detectors producing output signals based on received light;
   splitting a portion of the light reflected from the illuminated sample into two sample beams, the light from the illuminated sample carrying information about the sample;
   directing one sample beam to the first light sensitive detector and the other sample beam to the second light sensitive detector;
   passing one of the sample beams directed towards a light sensitive detector through a multivariate optical element;
   directing at least a portion of the light from the illumination source toward the first and second light sensitive detectors as a reference light;
   providing a temperature sensor in proximity to the first and second light sensitive detectors, the temperature sensor producing an output signal based on temperature;
   compensating the output signals produced by the first and second detectors based on the temperature output signal; and
   analyzing the compensated output signals produced by the first and second light sensitive detectors to determine temperature compensated illuminated sample information.

17. The method of claim 16, further comprising creating a vacuum around the light sensitive detectors and measuring the temperature within the vacuum.

18. The method of claim 16, further comprising:
   splitting the reference light into two reference beams, and directing one reference beam to the first detector and the other reference beam to the second detector; and
   passing one reference beam through a multivariate optical element.

19. The method of claim 18, further comprising modulating light from the illumination source.

* * * * *